Figure 1:
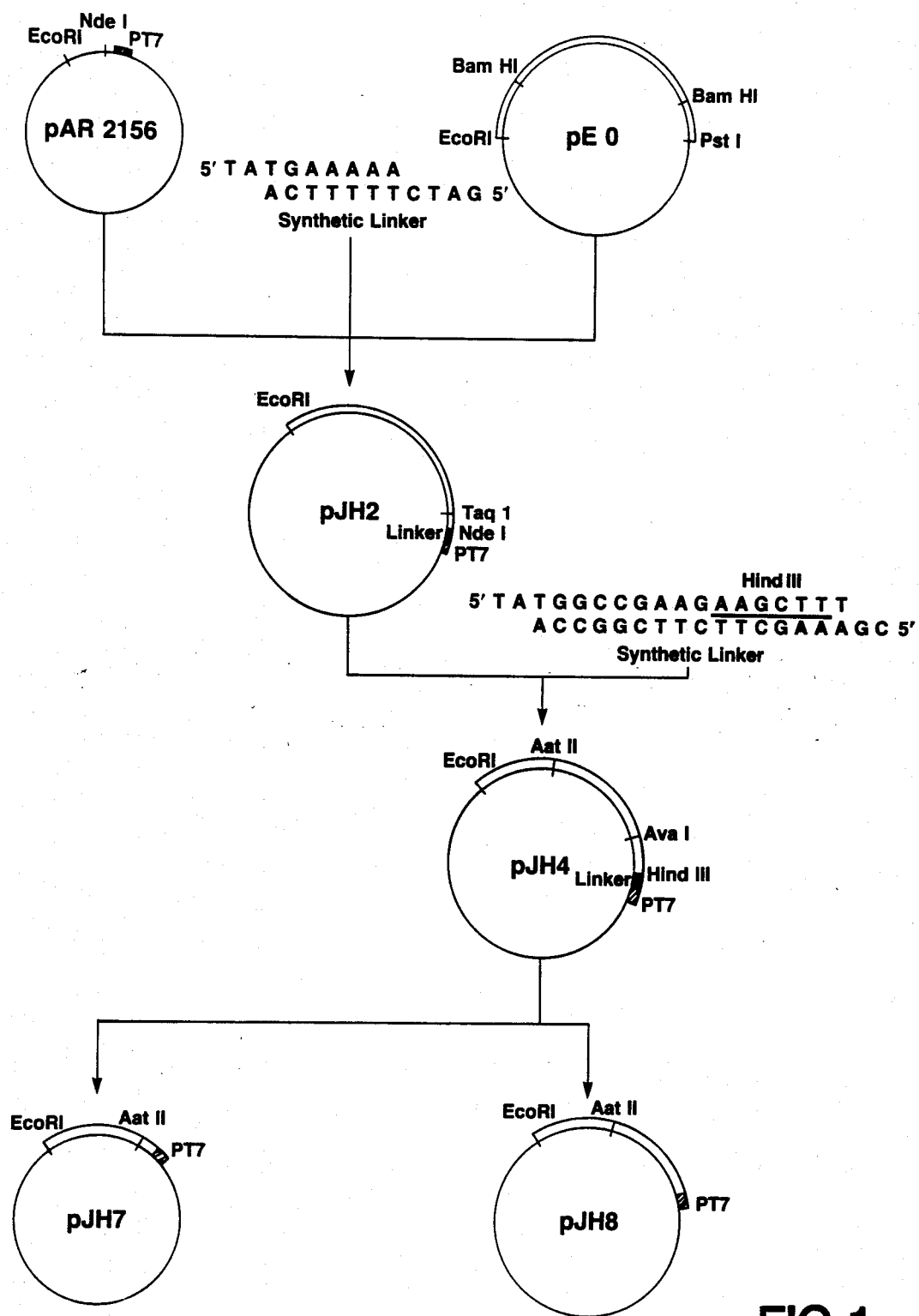

United States Patent [19]

Pastan et al.

[11] Patent Number: 4,892,827
[45] Date of Patent: Jan. 9, 1990

[54] RECOMBINANT PSEUDOMONAS EXOTOXINS: CONSTRUCTION OF AN ACTIVE IMMUNOTOXIN WITH LOW SIDE EFFECTS

[75] Inventors: Ira H. Pastan, Potomac; Sankar Adhya, Gaithersburg; David Fitzgerald, Bethesda, all of Md.

[73] Assignee: The United States of America as represented by the Department of Health and Human Services, Washington, D.C.

[21] Appl. No.: 911,227

[22] Filed: Sep. 24, 1986

[51] Int. Cl.⁴ .................. C12P 21/00; C12P 21/02; C12N 9/10; A61K 34/00

[52] U.S. Cl. .................... 435/193; 435/69.4; 435/69.52; 435/69.6; 435/69.7; 424/85.91; 424/88; 424/92; 424/91.5; 530/350; 530/351; 530/370; 530/395; 530/396; 935/14; 935/29; 935/56; 935/60; 935/65; 514/2; 514/6; 514/12

[58] Field of Search ............... 435/193, 172.3, 68, 435/70, 253, 317; 530/370, 350, 351, 395, 396; 424/85, 94.5, 88, 92; 514/2, 6, 8, 12

[56] References Cited

U.S. PATENT DOCUMENTS 4,545,985  10/1983  Pastan et al. ................. 424/85

OTHER PUBLICATIONS

Allured et al. *Proc Natl Acad Sci* vol. 83, pp. 1320–Mar. 1986, "Structure of exotoxin A of *Pseudomonas aeruginousa* at 3.0–Angstrom resolution".
Fitzgerald et al *Proc Natl Acad Sci* vol. 80, pp. 4134–4138, Jul. 1983 "Enhancement of toxicity of anti-transferrin receptor antibody *Pseudomonas exotoxin* conjugates by adenovirus".
Gray et al. *Proc Natl Acad Sci* May 1984 vol. 81, pp. 2645–2649 "Cloningt, nucleotide sequence, and expression in Escherichia coli of the exotoxin A structural gene of *Pseudomonas aeruginosa*".
Hwang et al. *Cell* vol. 48, pp. 129–136, Jan. 16, 1987, "Functional Domains of *Pseudomonas* Exotoxin Identified by Deletion Analysis of the Gene Expressed in *E. Coli*".
Kondo et al, 1988, Journal Biol. Chem. 263:9470–75.
Jinno et al, 1988, J. Biol. Chem. 263:13203–207.
Wozniak et al, 1988, PNAS, U.S.A. 85:8880–8884.
Chaudhary et al, 1988, PNAS, U.S.A. 85:2939–2943.
Montfont et al, 1987, J. Biol. Chem. 262:5398–5403.
Ribi et al, 1988, Science, 239:1272–1276.
Brandhuber et al, 1987, Science, 238:1707–1709.
Brandhuber et al, 1988, Proteins . . . 3:146–154.
McKay et al, 1982, J. Biol. Chem, 257:9518–24.
Weber et al, 1987, J. Mol. Biol. 198:311–326.
Bennett et al, 1978, PNAS, U.S.A. 75:4848–52.
Almassy et al, 1986, Nature, 323:304–309.

Primary Examiner—Robin Teskin
Attorney, Agent, or Firm—Mishrilal Jain

[57] ABSTRACT

Modified Pseudomonas exotoxins which comprise deletions in at least domain 1A are taught. The toxins exhibit reduced cytotoxicity.

10 Claims, 4 Drawing Sheets

RECOMBINANT PSEUDOMONAS EXOTOXINS: CONSTRUCTION OF AN ACTIVE IMMUNOTOXIN WITH LOW SIDE EFFECTS

BRIEF DESCRIPTION OF THE INVENTION

Large amounts of various modified forms of Pseudomonas exotoxin are produced. At least one of the modified forms (pJH8) of the exotoxin exhibits low toxicity to human or mouse cells by itself but retains its enzymatic activity and makes a very active cell specific immunotoxin with very low nonspecific cytotoxicity. All the constructs with low cytotoxic activity will be useful as vaccines to produce the antibodies to treat pseudomonas sepsis. In addition, the protein encoded by domain I alone could be administered directly to patients to treat pseudomonas sepsis because that domain would block toxin binding to cells. Clones containing domain II and particularly clone pJH12 can be fused to other toxins which have low activity (such as ricin A chain or pokeweed antiviral protein) to increase their cell-killing activity without increasing their nonspecific binding to cells.

BACKGROUND OF THE INVENTION

Toxins are extremely potent cell-killing agents that are responsible for many human diseases. Because of their high activity, these agents have been attached to monoclonal antibodies in order to form cytotoxic agents (immunotoxins) which specifically bind to target cells. These immunotoxins are, therefore, most useful in cancer therapy.

Pseudomonas exotoxin A (PE) is an extremely active monomeric protein (molecular weight 66Kd), secreted by *Pseudomonas aeruqinosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The intoxication process is believed to proceed by the following steps: First, PE binds to cells through a specific receptor on the cell surface. Next, the PE-receptor complex is internalized into the cell. Finally, PE is transferred to the cytosol where it enzymatically inhibits protein synthesis. The transfer process is believed to occur from an acidic compartment, since cellular intoxication is prevented by weak bases such as $NH_4+$, which raises the pH in acidic vesicles. Upon exposure to acidic conditions, the hydrophobic domain of PE enters into the membrane, resulting in the formation of a channel through which the enzymatic domain, in extended form, pass into the cytosol.

PE-containing immunotoxins are constructed by first reacting native PE with iminothiolane. This reaction serves both to introduce two new sulfhydryl groups used for coupling an antibody to the toxin, and to inactivate the binding of PE to its own receptor. This approach relies on the chemical inactivation of PE-binding sites in order to minimize undesirable side effects due to the binding of PE to cells with PE receptors. While this approach has been reasonably successful in producing a specific cell killing reagent in tissue culture and in tumor-bearing mice, it has not been possible to administer more than 2 ug of PE immunotoxin to a 20 gram mouse or 1 mg to a 3 kilogram monkey or 4 mg to an adult human, due to the toxic side effects of the immunotoxin. It is therefore desirable to be able to administer larger amounts of immunotoxins to achieve greater killing of tumor cells. The present invention fulfills this desire by providing an immunotoxin with high potency and low toxicity. Furthermore, to overcome the above-noted reliance on chemical inactivation of the PE binding sites, the present invention incorporates recombinant DNA techniques to clone the complete toxin gene (or segments of it) in order to express at high levels the full length toxin molecule (or portions of it) containing different functional domains, including one which lacks the cell binding domain. See Example 1 for a comparative examination of these clones.

Figure 2:
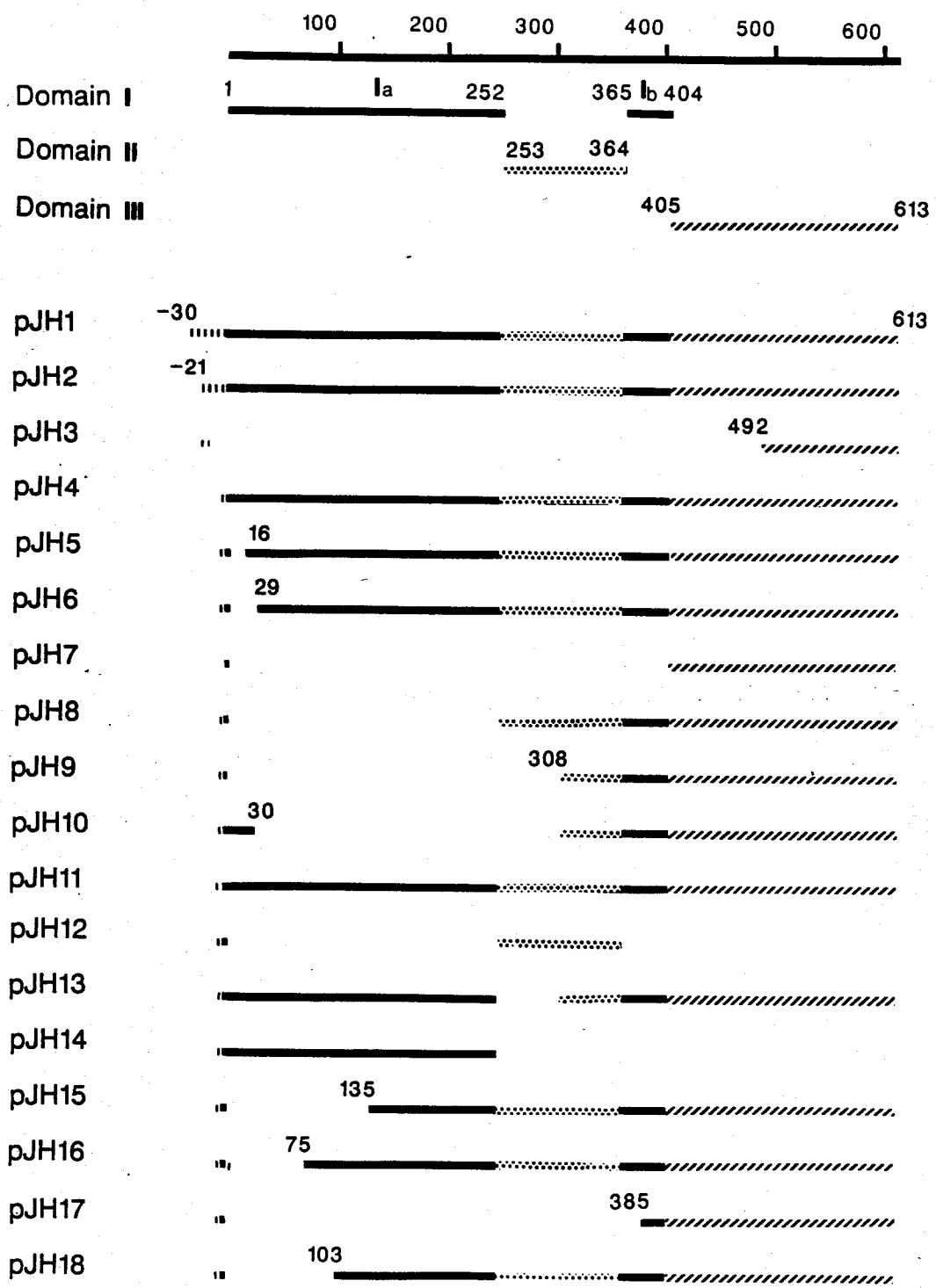

The three-dimensional structure of PE has been determined by x-ray crystallography. As shown in FIG. 2, the PE molecule contains three structurally distinct domains: Domain I contains amino acid residues 1 to 252 (Domain Ia), and 365 to 404 (Domain Ib); domain II contains amino acid residues 253 to 364; and domain III contains amino acid residues 405 to 613.

Plasmids have been constructed which express various portions of the PE molecule, providing the ability to correlate different structural domains with various functional activities and to determine (1) which portions of the molecule are responsible for cell recognition (binding), (structural domain I, amino acid 1–252); (2) which portion is required for enzymatic activity (ADP ribosylating activity, domain III plus a portion of domain Ib) (amino acid 385–613); (3) which portion is responsible for translocation across cell membrane (domain II). The evidence that structural domain Ia is involved in cell recognition is that proteins produced by plasmids without domain Ia but containing domain II, Ib and III, are not cytotoxic by themselves and do not show competitive inhibition of the cytotoxicity of intact toxins, whereas a plasmid encoding domain Ia, but missing other domains, blocked PE cytotoxicity of sensitive cells. PE from plasmids with a deletion of the first half of structural domain II exhibit both PE blocking activity and ADP-ribosylation activity, but these molecules lost all cell killing activity. Plasmids which encode only structural domain III produce large amounts of the protein, but lack detectable enzymatic activity (ADP-ribosylation). However, plasmids which encode all of structural domain III plus adjacent amino acids from structural domain Ib express large amounts of the protein and their ADP-ribosylation activity is high.

Based on the three dimensional structure of PE, plasmids have been constructed which express different portions of PE. The protein pattern of the cells expressing the different constructions was analyzed by SDS gel electrophoresis and the ADP ribosylating activity of the recombinant toxins was measured. Of these plasmids (described in Example 1) plasmid pJH8, containing amino acids 253 to 613 (Domains Ib, II, and III), and plasmid pJH17, containing amino acids 385 to 613 (Domain III, plus 20 adjacent amino acids from Domain Ib), are able to encode large amounts of modified PE exhibiting low toxicity to human cells, but remaining enzymatically very active.

Taken together, the plasmid patterns indicate that structural domain Ia is a receptor binding domain, that the first half of structural domain II is required for translocation of the toxin from a host cell's endocytic vesicle to the cytosol, and that structural domain III alone is not sufficient to express full ADP-ribosylation activity.

When administered to animals, PE characteristically produces death due to liver failure. Immunotoxins made with PE also attack the liver and, when given in large amounts, produce death due to liver toxicity. The experiments shown in Table III indicate that Domain Ia is responsible for cell binding and indicate that a PE molecule in which Domain Ia is deleted is less toxic to mice than native PE. The data shown in Example 4 support this conclusion, indicating that modified PE is at least 200-fold less toxic to mice than native PE. Example 5 shows that when the protein made by pJH8 is purified and coupled to an antibody to the human transferring receptor, an immunotoxin is created that is approximately as active as an immunotoxin containing native PE but is 100-fold less toxic on nontarget cells (mouse cells).

One aspect of the present invention, therefore, is that PE molecules with a deletion of Domain Ia are effective immunotoxins with diminished side effects including diminished liver toxicity.

DESCRIPTION OF THE FIGURES

FIG. 1 shows the construction of the plasmids of the present invention used for the expression of different domains of PE.

FIG. 2 is a simplified map of the different sized PE molecules produced as a part of the present invention.

FIGS. 3A and 3B show the effect of $PE_{45}$-HB21 and PE-HB21 on protein synthesis in human KB cells. $PE_{45}$ is the toxin protein lacking Domain I encoded by plasmid pJH8. Cells were incubated for 24 hours with the appropriate immunotoxin and then incubated with $^3H$-leucine for 1 hour. Incorporation of ($^3H$)-leucine into protein was measured. In panel 3B Swiss 3T3 cells were incubated for 24 hours with either native pseudomonas toxin (PE), native pseudomonas toxin coupled to HB21, $PE_{45}$ alone, or $PE_{45}$ coupled to HB21. Cells were exposed to these agents for 24 hours and then protein synthesis measured for 1 hour as above.

SPECIFIC DISCLOSURE OF THE INVENTION

In the preferred embodiment, the present invention is the production of a modified form of Pseudomonas Exotoxin (PE) wherein the modification results in an active immunotoxin. The modified toxin and the immunotoxin made from it have markedly diminished nonspecific toxicity on human and mouse cells in tissue culture and with greatly diminished toxicity in mice in vivo.

Genomic DNA is obtained by completely digesting a strain of *Pseudomonas aeruginosa* with EcoRI and PstI. Although any strain of P. aeruginosa is suitable for use in this invention, the preferred strain is PA103, a strain which produces a large amount of active toxin. DNA fragments ranging in size from 2.6 to 2.9 kb are isolated from the genomic DNA library, and ligated with a 2.7 kb DNA fragment from plasmid pUC13 cut with EcoRI and PstI. Plasmid pUC13 is commercially available from Boehringer Mannheim. A suitable host, preferably an *E. coli* strain, is then transformed with the ligated products (the preferred strain of E. coli is HB101, commercially available from Bethesda Research Laboratories). The 2.7 kb DNA fragment derived from ptoxETA, a plasmid which contains the PE structural gene, is used as a probe and plasmid DNA from several positive colonies were prepared and characterized by Southern blotting. The different sizes of recombinant PE are then expressed in a suitable host. A host which carries the bacteriophage T7 RNA polymerase gene in lysogenic and inducible form [BL21($DE_3$)]is preferred, and is obtainable from Dr. F. W. Studier at Brookhaven National Laboratories. Also preferred are plasmids which carry the bacteriophage late T7 promoter and $AMP^r$ and Shine-Dalgarno box—pAR2156, also obtainable from Dr. Studier.

As is shown in the Examples, the preferred plasmids are pJH8 and pJH17. pJH8 contains a DNA fragment of 5.1 kb and is capable of expressing Domains II, Ib, and III of PE. This plasmid is produced by partially cutting plasmid pJH4 with AvaI. The linearized DNA fragment is then completely cut with HindIII in order to obtain a 5.1 kb DNA fragment which has AvaI and HindIII sites at its ends. This fragment is then incubated with S1 nuclease to remove its cohesive ends, followed by ligation with T4 ligase to form plasmid pJH8.

Plasmid pJH17 contains a DNA fragment of 4.8 kb and is capable of expressing Domain III with the adjacent 20 amino acids of PE. This plasmid is produced by completely cutting plasmid pJH4 with HindIII and ApaI. The 4.8 kb DNA fragment is then isolated and incubated with Klenow DNA polymerase I and dNTP to fill the cohesive ends, followed by ligation with T4 ligase.

Expression of Recombinant Toxins in BL21($DE_3$).

BL21($DE_3$) containing plasmids for expression of different sizes of PE is cultured in LB broth with 50 ug Ampicillin/ml at 37° C. When absorbance at 650 nm reaches 0.3, IPTG (isopropyl beta-D-thio-galactopyranoside) is added to the culture at a final concentration of 1 mM. Cells are harvested 90 minutes later and analyzed for the amount of recombinant toxins by SDS-PAGE, immunoblotting, ADP-ribosylation, and cell killing experiments.

SDS-PAGE and Immunoblotting

Cells pellets are dissolved in Lemmli buffer. Samples are boiled for 5 minutes prior to application to a 0.1% SDS, 10% acrylamide slab gel. For immunoblotting, samples after electrophoresis are transferred to a nitrocellulose paper, followed by reaction with antibody to PE, then a second antibody (goat anti-rabbit) and staining. The antibody to PE is obtained by hyperimmunizing rabbits with glutaraldehyde (0.2%) reacted PE (250 ug of PE per injection). An IgG fraction was prepared for immunoblotting.

Assay of ADP-ribosylation Activity

Known procedures are used for assay of ADP-ribosylation activity. Briefly, rabbit reticulocyte preparations or wheat germ extracts enriched with elongation factor 2 (EF-2) are used as a source of EF-2. Assays (500 ul total volume) contain about 10 pmole of EF-2, 37 pmole of $^{14}C$-NAD (0.06 u Ci), 0.25 to 1.25 ug of PE and buffer (40 mM DTT, 1 mM EDTA, and 50 mM Tris, pH 8.1). Activity is measured as pmoles of NAD transferred to EF-2 in 30 minutes. A standard curve of known concentrations of PE is established and used to determine the activity of PE in extracts from *E. coli.* After incubation for 30 minutes at 37° C., 0.5 ml 12% TCA is added to each assay mixture. The assay mixtures are then set in an ice bath for 15 minutes, followed by centrifugation at 4° C., 3,000 xg for 10 minutes. The pellet is washed with 1 ml 6% TCA and centrifuged as above. The pellet is then measured for $_{14}C$ radioactivity in a liquid scintillation counter as the index of the ADP-ribosylation activity.

Cell Cytotoxicity Test

Tests of the cytotoxic activity of the modified PE are performed in NIH 3T3 cell cultures and human KB cells. NIH 3T3 cells or KB cells are seeded 24 hours prior to the cytotoxicity test in a 24-well tissue culture plate at a density of $2 \times 10^4$ cells per well. After incubation for 48 hours with various concentrations of PE or protein extracts isolated from BL21(DE$_3$) with plasmids which express different sizes of PE, the monolayers are stained with methylene blue to detect the surviving cells. The results are shown in Table 1.

Inhibition of Protein Synthesis

Assays for the inhibition of protein synthesis by PE or PE with extracts from BL21(DE$_3$)/pJH8 are performed in Swiss 3T3 cell cultures. Swiss 3T3 cells are seeded one day before assay in 24-well tissue culture plates at a density of $10^5$ cells per well. Cells are washed once by replacing media with DMEM and 0.2% BSA before adding PE (100 ng/ml) or PE (100 ng/ml) with extracts which contained an excess amount of different sizes of PE (Table 2). After 15 minutes at 37° C., the medium is then removed and replaced with fresh DMEM and 0.2% BSA. Four hours later, the rate of protein synthesis is assayed by adding [$^3$H] leucine to the medium (to a final concentration of 2–4 uCi/ml) for 1 hour.

In the preferred embodiment of the invention, the structural domain of the Pseudomonas exotoxin gene is inserted into a T7 expression vector downstream of the ribosome binding site and its accompanying ATG initiation codon (as shown in FIG. 1), as described above. To produce recombinant proteins, cells are grown at 370° C. to an $A_{650}$ =0.3. IPTG is then added at 1 mM to induce T7 RNA polymerase and incubated for 2 hours. A series of plasmids are produced, as shown in Example 1.

Next, a clone is constructed which encodes a PE molecule without a leader sequence (pJH4) and in which a methionine is placed adjacent to the alanine at the amino terminus of the processed form of native PE (Table 1). The protein produced by pJH4 is designated Met-PE. Large amounts of Met-PE are produced upon induction by IPTG, representing 20% of total cell protein. ADP ribosylating activity equivalent to 0.1 mg native PE is found in the supernatant, and 0.2 mg in the pellet per mg of total cell protein. The PE molecule produced by pJH4 differs from native PE molecules by the presence of one extra methionine residue at the amino-terminus.

pJH8, produced from pJH4 as noted above, expresses a protein in which most of Domain Ia is deleted (retaining only the added methionine and three amino acids at the amino terminus. Immunoblotting shows that this protein is 45 kd, and is expressed at a concentration of approximately 0.04 mg/mg cell protein. High ADP ribosylating activity is exhibited when urea and DTT is excluded from the reaction mixture. In contrast to native PE (where the addition of urea and DTT activates ADP ribosylating activity), the addition of urea and DTT to pJH8 reduces (by about 30%) ADP ribosylating activity.

Because the ADP ribosylating activity of PE resides in the carboxyl end of the molecule, plasmid pJH17, constructed from pJH4 (as noted above), was produced. This plasmid contains Domain III and 20 amino acids from Domain Ib. Extracts from this plasmid contain high levels of ADP ribosylating activity—equivalent to 0.06 mg PE (Table 1). By immunoblotting, a 31 kd protein is detected, present at a concentration of 0.03 mg/mg cell protein.

None of the plasmids produced by the above-noted process (and described in the Examples), except for pJH1, pJH2, and pJH4, exhibit significant cell killing ability, even though many of these exhibit high enzymatic activity (Table 1). These plasmids are shown to prevent inhibition of protein synthesis or cell killing by native PE by exposing cells for 15 minutes to native PE at 0.1 ug/ml in the presence of 3–5 ug/ml of various modified toxins. The data in Table III shows that plasmids expressing either Domain Ia alone, or Domain I, half of Domain II and Domain III prevent PE from inhibiting protein synthesis.

Animal Toxicity

Mice receiving native PE succumb due to liver destruction. The lethal dose for a 20 gram mouse is 0.1–0.2 ug. The data in Table IV shows that PE with a deletion of Domain Ia exhibits greatly diminished toxicity in mice. Mice were injected I.P. with either native PE or lacking Domain Ia. All mice receiving 1.0 ug of native PE and one-half receiving 0.2 ug PE were dead at 48 hours. Two of three mice receiving 50 ug of PE Ia died; all receiving 20 ug of PE Ia lived; and all mice receiving 5 ug PE Ia lived. Thus, PE Ia is more than 100 times less toxic on a weight basis than native PE.

Gene Fusions Using Recombinant Modified Pseudomonas Exotoxin

The gene for modified PE of this invention specifically contained in pJH8 was fused with DNA sequences encoding the human alpha transforming growth factor (a-TGF) or human interleukin 2 (IL-2). See Examples 7 and 8 for the specifics of these gene fusions. Modified PE is suitable for use in fusions with any peptide hormone, growth factor, or other polypeptide cell recognition protein for which a specific receptor exists on cells. A few examples include: insulin, glucagon, endorphins, growth hormone, melanocyte stimulating hormone, transferrin, bombesin, low density lipoprotein, luteinizing hormone, and asialoglycoproteins.

EXAMPLES

Example 1

As shown in Table 1, the process of the present invention was used to construct several plasmids containing fusions of the different sizes of PE structural gene and the T7 late promoter. pJH2 contains the intact PE structural gene with a segment coding for a modified leader sequence in front. pJH4 contains the intact PE structural gene with the addition of a methionine codon at the amino-terminus. pJH7 contains the gene encoding structural Domain III of PE (amino acid 405–613). pJH8 contains the gene encoding structural Domain II, Ib, and III of PE (amino acid 253–613. pJH13 encodes PE with a deletion of the first half of structural domain II encompassing amino acids 253–307. pJH14 encodes structural domain Ia of PE (amino acids 1–252). pJH17 encodes structural domain III with an additional adjacent sequence of 20 amino acids from Domain Ib (amino acids 385–613).

pJH1 was constructed by partially cutting the native PE (pE 0) with BamHI, and the linear form of DNA was eluted and completely cut with EcoRI. The 2.0kb DNA fragment derived from pE 0, which has BamHI and EcoRI at the two ends, was then inserted into pAR 2156, which had been completely cut with BamHI and EcoRI.

pJH2 was constructed by partially cutting pJH1 with BamHI. The linear form of DNA was isolated and completely cut with NdeI. The 610 kb DNA fragment was saved to construct pJH2 by ligating it with synthetic oligonucleotide duplex

```
5' T A T G A A A A A
      A C T T T T T C T A G 5'
``` pJH4 was constructed by partially cutting pJH2 with TaqI. The linearized DNA (610 kb) was isolated and completely cut with NdeI. The largest DNA fragment (5.9 kb) was separated and ligated with synthetic oligonucleotide duplex

```
5' T A T G G C C G A A G A A G C T T T
      A C C G G C T T C T T C G A A A G C 5'
```

(which contains a HindIII site--A A G C T T).
                                    T T C G A A pJH7 was constructed by partially cutting pJH4 with AatII. The linearized DNA fragment (5.9 kb) was then completely cut with HindIII. The 4.7 kb DNA fragment which has AatII and HindIII sites at its ends after separation was incubated with S1 nuclease to remove the cohesive ends, followed by ligation with T4 ligase.

pJH8 was constructed as described in the Specific Disclosure.

pJH13 was constructed by partially cutting pJH4 with AvaI. The linearized DNA fragment was then completely cut with EcoRI. The 4.7 kb DNA which has AvaI and EcoRI cut at both ends was incubated with S1 to remove cohesive ends (DNA fragment 1). pJH4 was partially cut with SalI. The linearized DNA fragment was then completely cut with EcoRI. The 1.0 kb DNA fragment which has SalI and EcoRI sites at the ends was incubated with Klenow DNA polymerase I and dNTP to fill the cohesive ends (DNA fragment 2). DNA fragment 1 (4.7 kb) and DNA fragment 2 (1.0 kb) were ligated at 4° overnight.

pJH14 was constructed by partially cutting pJH4 with AvaI. The linearized DNA fragment was then completely cut with EcoRI. The 4.7 kb DNA which has AvaI and EcoRI sites at its ends was incubated with S1 to remove the cohesive end, followed by ligation with T4 ligase.

pJH17 was constructed as described in the Specific Disclosure.

Example 2

The amount and activity of the recombinant toxins (produced by the plasmids described in Example 1) were measured by SDS-PAGE, ADP-ribosylation, and cell killing ability. The results are tabulated in Table 1.

EXAMPLE 3

Determinations were made of the sizes of the protein and the domains present in various constructions of the present invention. The results are shown in Table 2.

Example 4

The effect of various deletions on cell protein synthesis was determined, in the presence and absence of native PE. The results are shown in Table 3. Structural Domain Ia (pJH14) and structural domain I, half of II, and III (pJH13) were extracted from the pellet of the sonicated cells with 8M urea. 10 ul of each extract equivalent to 3-5 ug of recombinant proteins was used in each assay. Structural II, Ib, and III (pJH8) were present in the supernatant of the sonicated BL21(DE$_3$)/pJH8 cells. 10 ul of extract equivalent to 2 ug of recombinant toxin was used. Cells were treated as indicated in Table 3 for 15 minutes with and without native PE at 0.1 ug/ml followed by 1 ml DMEM washing; incubated for 4 hours in DMEM and 0.2% BSA, then incubated with $^3$H-leucine for 1 hour.

Example 5

As shown in Table 4, the dose causing death in mice was determined by injecting Balb/c mice I.P. with various amounts of PE contained in 1.0 ml of sterile saline and 10 mgs/ml sterile human albumin. The animals were monitored daily for two weeks. All deaths occurred at 48 hours.

Example 6

Figure 3A:
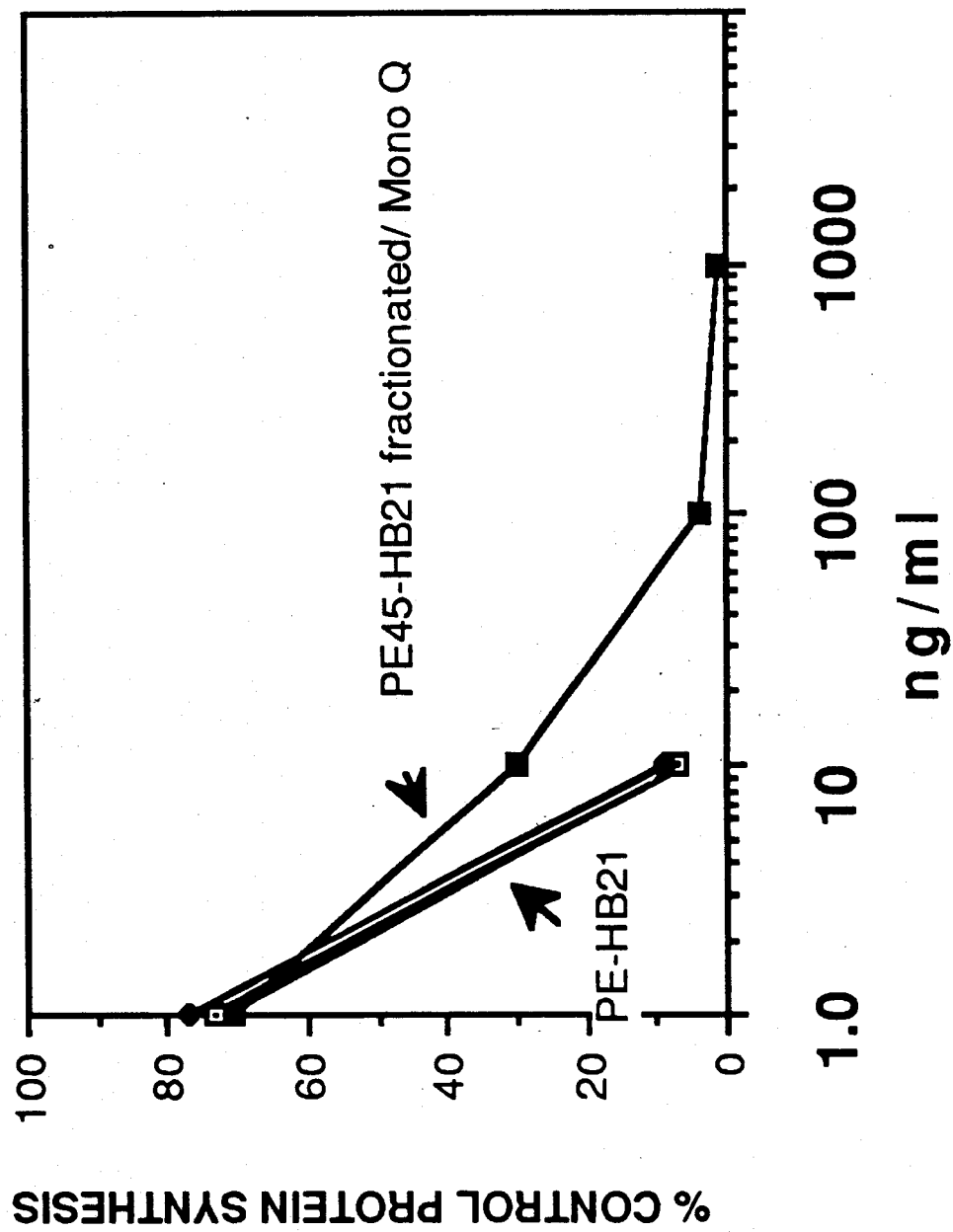
Figure 3B:
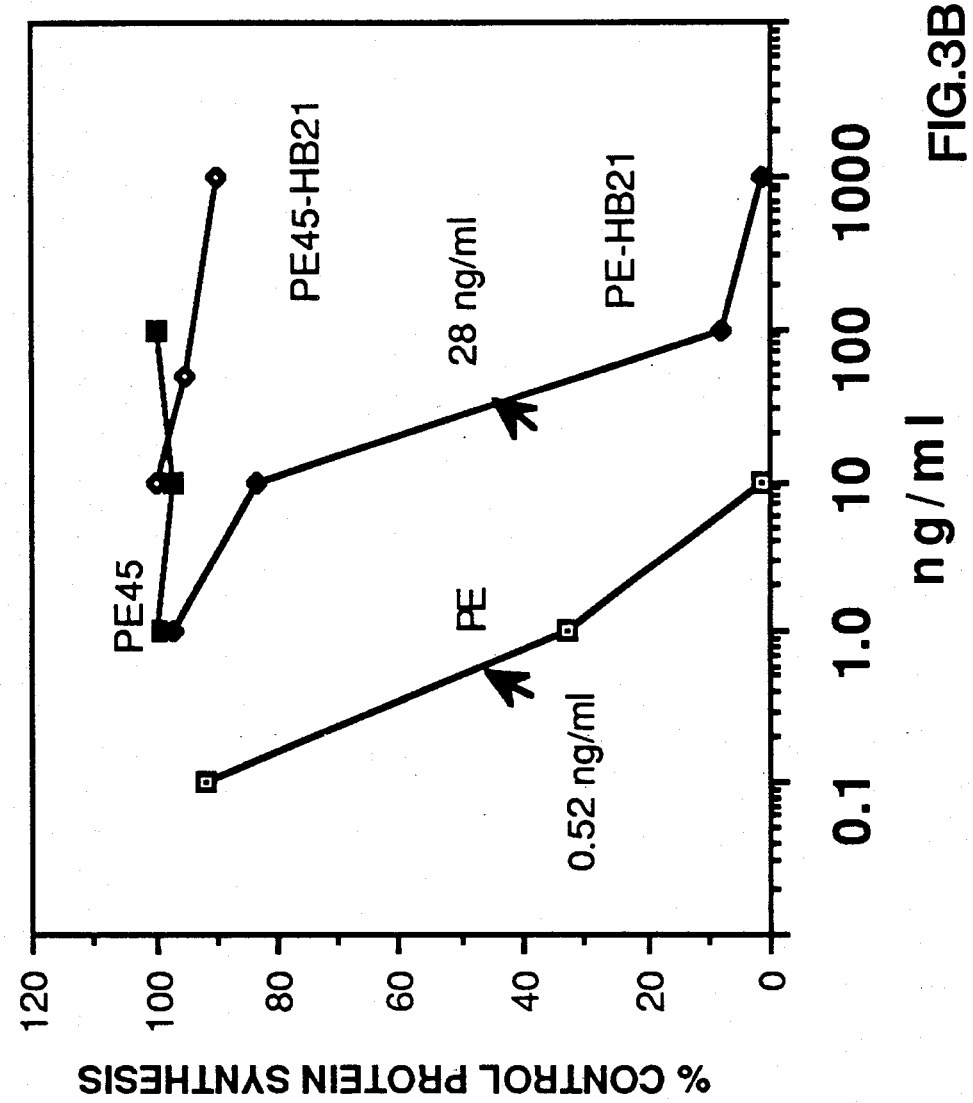

As shown in FIGS. 3A and 3B an immunotoxin composed of the 45 kD protein produced by pJH8 conjugated by a disulfide bond to an antibody to the human transferrin receptor (PE$_{45}$-HB21) kills human cells expressing the transferrin receptor (ID$_{50}$ 3 ng/ml). It has little or no effect on mouse cells which do not express the human transferrin receptor at 1000 ng/ml, whereas native PE conjugated by a sulfide bond to HB21 non-specifically kills mouse cells at an ID$_{50}$ of 29 ng/ml. The data in FIG. 3 indicate the non-specific toxicity of PE$_{45}$-HB21 is 100-fold less than PE-HB21.

Example 7

Construction of alpha Transforming Growth Factor-PE fusion gene pJH8 was treated with Tth 111I and SphI to construct a smaller plasmid pVC8 which has fewer AvaII sites. pVC8 was partially cut with AvaII and ligated to a synthetic oligonucleotide (30 bp) which contains a StuI site, a Tth 111I site, and a stop codon in order to create pVC31. pVC31 was cut with Tth 111I, and filled in with a Klenow fragment, a fragment of DNA polymerase, and ligated to a blunt ended clone containing the alpha-TGF gene (pVC 33). The alpha-TGF DNA, p-hTGF-10-925 [Derynck etal, Cell, 38:287-297 (1984)] was cut with EcoRI and BglI to give a 322 bp fragment which was isolated and cut with Fnu 4HI and treated with T4 polymerase to give a 152 bp fragment which in turn was ligated to pVC31 to create PE-alpha-TGF fusion gene. When expressed in E. coli B121, this plasmid produces a protein that reacts with antibodies to alpha-TGF and to PE and has a molecular weight of 51,000.

Example 8

Construction of IL-2-PE Fusion Gene pVC8 was cut with AvaII at position 1190, the 3.6 fragment isolated, its single stranded ends filled with Klenow enzyme, and dephosphorylated to produce fragment I. Clone PST-5 [Gallo et al, PNAS, 81:2543-2547 (1984)] was cut with PstI to produce a 1 kD fragment of IL-2 which was then cut with Bsp 1286 at positions 105 and 669 and treated with T4 polymerase to fill up the ends. The 564 bp fragment was ligated to fragment I to create pHL-1 and transformed into BL21 expression cells. Upon induction, a 60 kD protein was produced that reacts with antibodies to IL-2 and to PE, and contains ADP-ribosylating activity.

TABLE 1

Summary of the Amount and Activity of the Recombinant Toxins Measured By SDS-PAGE, ADP-ribosylation, and Cell Killing Experiments

| | Amount of PE per mg of Cellular Protein | | | | |
|---|---|---|---|---|---|
| | Measured by SDS-PAGE (mg) | Measured by ADP-ribosylation* (units) | | Measured by Cell Killing (units) | |
| | Total | Sup. | Pellet | Sup. | Pellet |
| pJH1 | 0.20[a] | N.D. | N.D. | N.D. | N.D. |
| pJH2 | 0.20[a] | N.D. | N.D. | N.D. | N.D. |
| pJH3 | degraded | <0.001 | <0.001 | N.D. | N.D. |
| pJH4 | 0.20[a] | 0.10 | 0.20 | <0.001 | 0.2 |
| pJH5 | degraded | 0.15 | 0.02 | N.D. | N.D. |
| pJH6 | degraded | <0.001 | <0.001 | N.D. | N.D. |
| pJH7 | 0.25[o,a] | <0.001 | <0.001 | <0.001 | <0.001 |
| pJH8 | 0.04[o,n] | 0.66 | 0.04 | <0.001 | <0.001 |
| pJH9 | 0.15[a] | 0.40 | 0.20 | <0.001 | <0.001 |
| pJH10 | 0.15[a] | 0.40 | 0.15 | <0.001 | 0.001 |
| pJH11 | 0.25[a] | <0.001 | <0.001 | <0.001 | <0.001 |
| pJH12 | <0.01[o,n] | <0.001 | <0.001 | N.D. | N.D. |
| pJH13 | 0.01 | 0.25 | 0.20 | <0.001 | <0.001 |
| pJH14 | 0.30[a] | <0.001 | <0.001 | <0.001 | <0.001 |
| pJH15 | 0.10[a] | 0.18 | 0.30 | <0.001 | <0.001 |
| pJH16 | <0.01[n] | 0.02 | N.D. | N.D. | N.D. |
| pJH17 | 0.03[o,n] | 0.06 | <0.001 | <0.001 | <0.001 |
| pJH18 | <0.01[n] | 0.02 | N.D. | N.D. | N.D. |

*1 unit of ADP-ribosylation or cell killing activity is equivalent to the activity from 1 mg of native PE.
N.D. = not determined
[a]aggregated
[o]positive by Western
[n]not visible on SDS PAGE

TABLE 2

| Construction | Domain Present | Protein Size |
|---|---|---|
| pJH4 | met, I, II, III | 68 kd |
| pJH7 | III | 28 kd |
| pJH8 | II, Ib, III | 45 kd |
| pJH13 | I, half of II, III | 63 kd |
| pJH14 | Ia | 32 kd |
| pJH17 | 20 a.a. of Ib, III | 31 kd |

TABLE 4

| Toxin | Dose (ug) | Deaths |
|---|---|---|
| PE | 50 | 2/3 |
| PE | 20 | 0/3 |
| PE | 5 | 0/3 |
| PE | 10 | 2/3 |
| PE | 1.0 | 3/3 |
| PE | 0.3 | 3/3 |
| PE | 0.2 | 1/2 |
| PE | 0.1 | 0/3 |

TABLE 3

| | 3H—leucine in corporation (cpm × $10^3$) | |
|---|---|---|
| Domain Tested | without PE | with PE (I, II, III) |
| none | 11.2 ± .1 | 2.3 ± .2 |
| Ia | 11.5 ± .15 | 9.4 ± .3 |
| II, Ib, & III | 11.7 ± .15 | 2.4 ± .2 |
| I, ½ II, III | 10.7 ± .15 | 9.2 ± .2 |
| 8 M urea (10 ul) | 11.1 ± .1 | 2.9 ± .2 |

Statement of Deposit

The following plasmids have been deposited in the American Type Culture Collection in Rockville, Md., under the respective ATCC numbers, prior to the filing of this application, and at issuance of this application into a patent will be maintained for a term of thirty (30) years from the date of deposit or five (5) years after the last request for such deposit or for the effective life of the patent, whichever is longest. The deposits will be replaced if the cultures mutate or become nonviable during the term of the deposit:

| | |
|---|---|
| pJH12 | ATCC 67205 |
| pHL-1 | ATCC 67206 |
| pVC33 | ATCC 67207 |
| pJH8 | ATCC 67208 |
| pJH14 | ATCC 67209 |

We claim:

1. A modified Pseudomonas exotoxin which comprises ADP ribosylating activity and the ability to translocate across a cell membrane; wherein the exotoxin comprises a deletion in the receptor binding domain Ia of the native toxin sufficient to render the modified toxin less toxic to human or animal cells in vitro and less toxic to the liver when administered in vivo relative to an unmodified Pseudomonas exotoxin.

2. The modified exotoxin of claim 1, being covalently bound to a cell recognition protein which binds to a receptor on the targeted cell membrane and selectively kills cells bearing said receptor.

3. A composition comprising a cytotoxic amount of the exotoxin of claim 2.

4. A method for achieving targeted cytotoxicity, comprising contacting cells targeted to be killed, with a cytotoxic amount of the composition of claim 3, said targeted cells being those having receptors to which said recognition protein binds, but the composition being without cytotoxicity to cells which comprise PE receptors and lack receptors for the cell recognition protein.

5. The modified exotoxin of claim 2 wherein said cell recognition protein is selected from the group consisting of an antibody, a peptide hormone, a growth factor and a cytokine.

6. The exotoxin of claim 5 wherein said cell recognition protein is an antibody.

7. The exotoxin of claim 5 wherein said growth factor is a-TGF.

8. The exotoxin of claim 5 wherein said cytokine is interleukin-2.

9. The exotoxin of claim 6 wherein said antibody is antitransferin receptor antibody.

10. The modified exotoxin of claim 1 produced by employing the plasmid of ATCC deposit number 67206, 67207, or 67208 under conditions permissive for expression of the toxin.

* * * * *